United States Patent [19]

Kray

[11] 3,948,974

[45] Apr. 6, 1976

[54] ESTERIFICATION OF ORTHOPHTHALIC ACID WITH OLEFIN

[75] Inventor: Louis R. Kray, Novato, Calif.

[73] Assignee: Chevron Research Company, San Francisco, Calif.

[22] Filed: Aug. 20, 1969

[21] Appl. No.: 851,754

[52] U.S. Cl. ...... 260/475 R; 260/471 R; 260/473 R; 260/475 FR
[51] Int. Cl.² ........................................ C07C 69/80
[58] Field of Search .................................. 260/475 R

[56] References Cited
UNITED STATES PATENTS 2,198,046  4/1940  Vierling et al. ...................... 260/475

3,474,131  10/1969  Schmerling ......................... 260/475

Primary Examiner—Lorraine A. Weinberger
Assistant Examiner—Jane S. Myers
Attorney, Agent, or Firm—G. F. Magdeburger; John Stoner, Jr.

[57] ABSTRACT

Diesters of orthophthalic acid are obtained by reacting an olefin of at least six carbon atoms with orthophthalic acid in the presence of a boron trifluoride catalyst.

3 Claims, No Drawings

ESTERIFICATION OF ORTHOPHTHALIC ACID WITH OLEFIN

BACKGROUND OF THE INVENTION

It has been generally accepted that orthophthalic acid does not react with olefins having more than 5 carbon atoms. For example, in U.S. Pat. No. 2,975,210, this nonreactivity of phthalic acid toward olefins made it necessary to resort to preliminary formation of orthophthalic acid ester by reaction of orthophthalic anhydride and a primary alcohol, the orthophthalic acid ester then being reacted with olefin to give the desired ester. Such nonreactivity of orthophthalic acid with olefins was also the subject of an article in Industrial and Engineering Chemistry, Product Research and Development, Volume 2, dated 1963, at page 133.

SUMMARY OF THE INVENTION

It has now been found that disecondary alkyl orthophthalates are effectively prepared by the process which comprises reacting orthophthalic acid with an olefin of from 6 to 12 carbon atoms in the presence of a boron trifluoride catalyst at temperatures in the range of 50°C. to 90°C.

DESCRIPTION OF THE PREFERRED EMODIMENTS

Although orthophthalic acid is preferred, the acids may be any of the aromatic 1,2-dicaroxylic acids or substituted aromatic 1,2-dicarboxylic acids. Such compounds would have the general formula

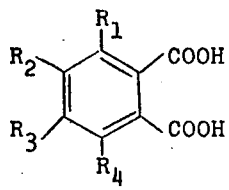

wherein $R_1$, $R_2$, $R_3$, and $R_4$ may be the same or different, H, alkyl of 1 to 20 carbon atoms, alkoxy of 1 to 20 carbon atoms, halogen, carboxy, nitro; $R_2$ and $R_3$ may be the same or different aromatic groups; $R_1$ and $R_2$ or $R_2$ and $R_3$ may represent a 3 or 4 carbon methylene bridge, or a 4 carbon-4 hydrogen bridge.

The olefins which are reacted with orthophthalic acid in accordance with the process of the present invention contain at least 6 carbon atoms, preferably from about 6 to about 12 carbon atoms. The olefins useful in this process may be either terminal or internal olefins. The preferred olefins are essentially unbranched straight chain olefins. Terminal olefins include 1-hexene, 1-butene, 1-dodecene and the like. Internal olefins include 3-hexene, 4-octene, 2-nonene, 5-dodecene, and the like.

The reaction of an olefin and orthophthalic acid is catalyzed by boron trifluoride. The reaction mixture of olefin, orthophthalic acid and catalyst is heated at temperatures in the range of about 50°C. to about 90°C. The reaction ordinarily takes from about 2 to about 6 hours.

The reaction of olefin and orthophthalic acid in accordance with the invention may be carried out at atmospheric conditions or under vacuum or pressure. For present purposes autogenous pressures are preferred.

The proportions of olefin and orthophthalic acid are generally in stoichiometric amounts. However, excess amounts of olefin are preferred, followed by separation and recycle of unreacted olefin.

The catalyst for this reaction is boron trifluoride. It may be used alone or in the form of a complex compound. Boron trifluoride complexes are well known catalysts (ref. "Boron Trifluoride and Its Derivatives" by H. S. Booth and D. R. Martin, published by J. Wiley and Sons, New York, 1949, page 170) and are usually formed by adding boron trifluoride to the complexing agent. The preferred catalyst for this process is the boron trifluoride etherate complex. The low molecular weight etherates, e.g. methyl or ethyl, are particularly preferred.

The products of the reaction are readily purified by conventional means including distillation, extraction and the like.

The following examples illustrate the process according to the present invention. These examples in no manner are intended to limit the invention described. The proportions are on a weight basis unless otherwise indicated.

EXAMPLE 1

Preparation of Disecondary Octyl Orthophthalate

A reaction vessel was charged with 8.3 g. (0.05 mole) of orthophthalic acid and 22 g. (0.10 mole) of 1-octene. To these reactants, 2 g. of boron trifluoride etherate catalyst was added. The reactants and catalyst were heated at a temperature of from about 60°C. to 70°C. for a period of about 4½ hours. Water, 5 ml., was added to the reaction mixture to hydrolyze the catalyst. Then the reaction mixture was extracted two times with 25 ml. portions of 25% aqueous sodium hydroxide. After drying, the organic layer was distilled. An 82% yield of disecondary octyl orthophthalate was obtained at a 45% conversion of orthophthalic acid.

Other examples were carried out in a manner similar to that of Example 1. The reaction conditions and the results thereof are given below:

| Ex. No. | Olefin | Grams | Catalyst | Grams | Acid | Grams | Time Hrs. | Temp. °C | Conversion of Acid % | Yield[1] % |
|---|---|---|---|---|---|---|---|---|---|---|
| 2 | 1-decene | 28.4 | BF$_3$.etherate | 2.0 | o-phthalic | 8.3 | 4 | 64–65 | 14 | 100 |
| 3 | 1-nonene | 25.2 | " | " | " | " | " | " | 23 | 36 |
| 4 | 1-octene | 33.6 | BF$_3$ | " | trimellitic | 10.5 | " | " | 8 | 6 |
| 5 | 1-hexene | 33.6 | BF$_3$.etherate | " | o-phthalic | 8.3 | " | " | 10 | 65 |
| 6 | 1-octene | 44.0 | BF$_3$ | sat'd | " | 16.6 | " | 60–70 | 11 | 62 |
| 7 | 2-octene | 44.0 | BF$_3$.etherate | 4.0 | " | 16.6 | 5 | " | 27 | 49 |

[1] Yield based on converted acid.

While the character of this invention has been described in detail with numerous examples, this has been done by way of illustration only and without limitation of the invention. It will be apparent to those skilled in the art that modifications and variations of the illustrative examples may be made in the practice of the invention within the scope of the following claims.

What is claimed is:

1. The process which comprises reacting orthophthalic acid with an olefin of from about 6 to 12 carbon atoms in the presence of a boron trifluoride etherate catalyst at temperatures in the range of 50°C. to 90°C. for about 2 to 6 hours.

2. The process of claim 1 in which the olefin is 1-octene.

3. The process of claim 1 in which the catalyst is a boron trifluoride ethyl etherate complex.

* * * * *